United States Patent
Goto et al.

(10) Patent No.: US 12,121,386 B2
(45) Date of Patent: Oct. 22, 2024

(54) X-RAY COMPUTED TOMOGRAPHY APPARATUS, MEDICAL IMAGE DISPLAY APPARATUS, AND MEDICAL IMAGE DISPLAY METHOD

(71) Applicant: CANON MEDICAL SYSTEMS CORPORATION, Otawara (JP)

(72) Inventors: Takahiro Goto, Utsunomiya (JP); Soichiro Iwabuchi, Nasushiobara (JP); Yasutaka Shindo, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 260 days.

(21) Appl. No.: 17/695,103

(22) Filed: Mar. 15, 2022

(65) Prior Publication Data
US 2022/0313191 A1 Oct. 6, 2022

(30) Foreign Application Priority Data

Apr. 2, 2021 (JP) ................. 2021-063313

(51) Int. Cl.
*A61B 6/00* (2024.01)
*A61B 6/03* (2006.01)
*A61B 6/04* (2006.01)
*A61B 6/46* (2024.01)

(52) U.S. Cl.
CPC ............ *A61B 6/5205* (2013.01); *A61B 6/032* (2013.01); *A61B 6/0407* (2013.01); *A61B 6/0487* (2020.08); *A61B 6/461* (2013.01)

(58) Field of Classification Search
None
See application file for complete search history.

(56) References Cited

U.S. PATENT DOCUMENTS

| | | | |
|---|---|---|---|
| 2020/0205748 A1 | 7/2020 | Pautsch et al. | |
| 2020/0279652 A1* | 9/2020 | Nenoki | G16H 30/40 |
| 2021/0169432 A1* | 6/2021 | Liu | G06T 7/73 |

FOREIGN PATENT DOCUMENTS

| | | | |
|---|---|---|---|
| JP | 2005-2619320 A | 9/2005 | |
| JP | 2014-004234 A | 1/2014 | |
| JP | 2015-130973 A | 7/2015 | |
| JP | 2017-120636 A | 7/2017 | |
| JP | 2017-202321 A | 11/2017 | |
| JP | 2020-121104 A | 8/2020 | |

OTHER PUBLICATIONS

Japanese Office Action dated Sep. 10, 2024, issued in Japanese Patent Aplication No. 2021-063313 (with English translation, documents 15-18 are cited therein).

* cited by examiner

*Primary Examiner* — Hoon K Song
(74) *Attorney, Agent, or Firm* — Oblon, McClelland, Maier & Neustadt, L.L.P.

(57) ABSTRACT

An X-ray computed tomography apparatus includes processing circuitry and a display. The processing circuitry is configured to perform reconstruction processing to raw data generated by a scan of a subject to reconstruct a medical image, and determine a posture of the subject at the time of the scan, according to an imaging condition reflecting an examination order for the scan. The display displays the medical image in association with information as to the posture.

10 Claims, 12 Drawing Sheets

FIG.4

| BODY-POSITION INFORMA-TION | No. 801 | TUBE VOLTAGE 802 | TUBE CURRENT 803 | SCAN TIME 804 | ... |
|---|---|---|---|---|---|
| | 1 | 100 kV | 300 mA | 0.5 s | ... |
| | 2 | 100 kV | 200 mA | 0.5 s | ... |
| | 3 | 100 kV | 500 mA | 1 s | ... |
| | 4 | 100 kV | 300 mA | 2 s | ... |

X-RAY COMPUTED TOMOGRAPHY APPARATUS, MEDICAL IMAGE DISPLAY APPARATUS, AND MEDICAL IMAGE DISPLAY METHOD

CROSS-REFERENCE TO RELATED APPLICATION

This application is based upon and claims the benefit of priority from Japanese Patent Application No. 2021-063313, filed on Apr. 2, 2021; the entire contents of which are incorporated herein by reference.

FIELD

Embodiments described herein relate generally to an X-ray computed tomography apparatus, a medical image display apparatus, and a medical image display method.

BACKGROUND

Traditionally, an X-ray computed tomography (CT) apparatus (hereinafter, X-ray CT apparatus) scans a subject while being laid on a couch. Basic body positions of the subject lying on the couch include a spine position and a prone position. Scan data has added thereto supplementary information which is prepared on the premise that a subject body position be a decubitus position. Further, in terms of display of medical images generated by the X-ray CT apparatus, a subject body position is also considered to be a decubitus position.

Meanwhile, X-ray CT apparatuses capable of scanning a subject in an upright position have become available in recent years. Such an X-ray CT apparatus may scan a subject in different body positions such as decubitus, upright, and seated by changing the position and orientation of the gantry, for example. In such a case, with respect to scan data as well as the supplementary information and the image display defined assuming the subject body position as decubitus, the operator may be required to input new body-position and posture information of a captured subject for storage. That is, the traditional X-ray CT apparatuses include body-position information of a subject in a decubitus position but no body-position information thereof in different positions such as an upright position and a seated position. In the case of using the X-ray CT apparatus capable of scanning a subject in different positions and postures as upright, decubitus, and seated, the operator may face difficulty in determining in what body position or posture the subject has been scanned.

BRIEF DESCRIPTION OF THE DRAWINGS

FIG. 4 illustrates a display of posture-related information together with a scan-plan list in the first embodiment by way of example;

DETAILED DESCRIPTION

Figure 1:
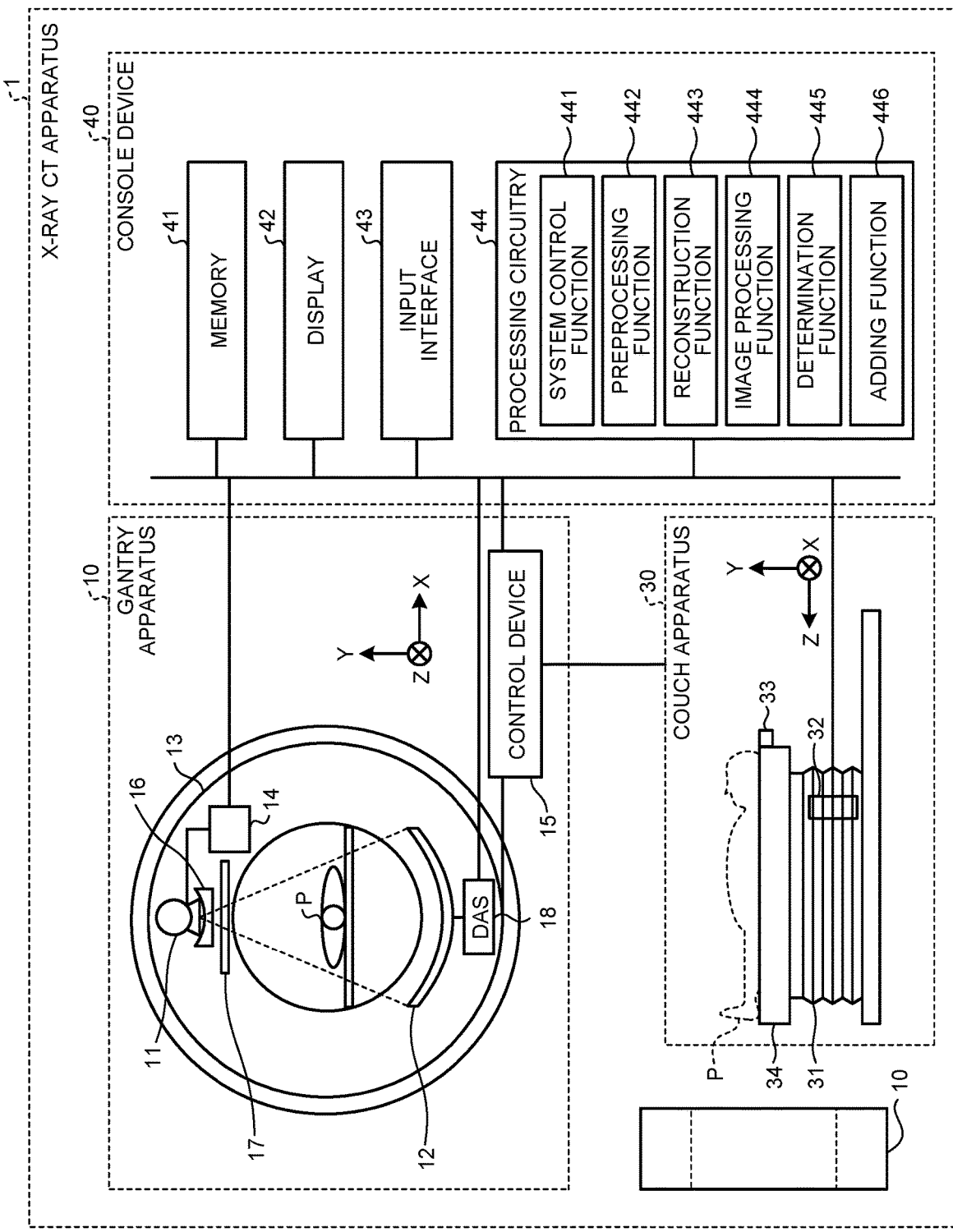
FIG. 1 illustrates an exemplary structure of an X-ray CT apparatus according to a first embodiment.

According to an embodiment to be described below, an X-ray computed tomography apparatus includes processing circuitry and a display. The processing circuitry is configured to perform reconstruction processing to raw data generated by a scan of a subject to reconstruct a medical image, and determine a posture of the subject at the time of the scan, according to an imaging condition reflecting an examination order for the scan. The display displays the medical image in association with information as to the posture.

Hereinafter, an X-ray computed tomography (CT) apparatus (hereinafter, X-ray CT apparatus), a medical image display apparatus, and a medical image display method according to some embodiments will be described with reference to the accompanying drawings. In the following embodiments, parts, portions, elements, or functions denoted by the same reference numerals are considered to perform same or similar operation, and an overlapping explanation thereof will be omitted when appropriate.

First Embodiment

FIG. 1 illustrates an exemplary structure of an X-ray CT apparatus 1 according to a first embodiment. As illustrated in FIG. 1, the X-ray CT apparatus 1 includes a gantry apparatus 10, a couch apparatus 30, and a console device 40. In the present embodiment a Z-axis direction, an X-axis direction, and a Y-axis direction are defined. The Z-axis direction corresponds to the longitudinal direction of the rotation axis of a rotational frame 13 in a non-tilted state. The X-axis direction is a direction from the center of rotation toward a support rod supporting the rotational frame 13 and orthogonal to the Z-axis direction. The Y-axis direction is orthogonal to the X-axis direction and the Z-axis direction. Although FIG. 1 depicts more than one gantry apparatus 10 for the sake of convenience, the X-ray CT apparatus 1 includes one gantry apparatus 10 in reality.

The X-ray CT apparatus 1 illustrated in FIG. 1 includes the couch apparatus 30 so as to be able to scan a subject P in a decubitus position, however, the X-ray CT apparatus 1 of the first embodiment may not include the couch apparatus 30. As an example, the X-ray CT apparatus 1 may include the gantry apparatus 10 of a substantially cylindrical form with a vertically extending opening. In such a case the X-ray CT apparatus 1 scans the subject P in an upright position, therefore, it can omit the couch apparatus 30. Such an X-ray CT apparatus is referred to as an upright CT apparatus. The gantry apparatus 10 may be changeable the rotation axis of the rotational frame 13, for example, between a horizontal direction and a vertical direction, to allow scanning of the subject P in any body position, i.e., decubitus, upright, and any other positions. The couch apparatus 30 is moved along with the displacement of the gantry apparatus 10. As an example, the couch apparatus 30 is retreated in the upright state or during displacement of the gantry apparatus 10 while in the decubitus state of the gantry apparatus 10 the couch apparatus 30 is moved to the position illustrated in FIG. 1. Further, the gantry apparatus 10 may be changeable the rotation axis of the rotational frame 13, for example, between the horizontal direction and the vertical direction, to allow scanning of the subject P in an oblique position where the body position of the subject P is obliquely tilted with respect to a horizontal plane. In this case the couch apparatus 30 is appropriately tilted in accordance with the displacement of the gantry apparatus 10, to avoid interference with the gantry apparatus 10. As described above, the X-ray CT apparatus 1 of the first embodiment can include the gantry apparatus 10 of any form.

The gantry apparatus 10 and the couch apparatus 30 operate in accordance with an operator's manipulation via the console device 40 or via an operational unit included in the gantry apparatus 10 or the couch apparatus 30. The gantry apparatus 10, the couch apparatus 30, the console device 40 are mutually connected in a wireless or wired manner to be communicable with one another.

The gantry apparatus 10 includes an imaging system which irradiates the subject P with X-rays and detects X-rays having transmitted the subject P to acquire projection data from X-ray detection data. The gantry apparatus 10 includes an X-ray tube 11, an X-ray detector 12, the rotational frame 13, an X-ray high voltage apparatus 14, a control device 15, a wedge 16, a collimator 17, and a data acquisition system (DAS) 18.

The X-ray tube 11 is a vacuum tube to be applied with a high voltage and supplied with a filament current from the X-ray high-voltage apparatus 14 to generate X-rays by emitting thermoelectrons from a negative pole (filament) to a positive pole (target). The X-rays are generated as a result of collision between the thermoelectrons and the target. The X-rays are generated at the focal point of the tube 11, pass through an X-ray emission window thereof, and are formed into, for example, a cone beam via the collimator 17 and emitted to the subject P. Examples of the X-ray tube 11 include a rotating anode X-ray tube that generates X-rays by emitting thermoelectrons onto a rotating positive pole (anode).

The X-ray detector 12 detects an X-ray emitted from the X-ray tube 11 and having passed through the subject P and outputs an electric signal corresponding to an amount of the X-ray to the DAS 18. The X-ray detector 12 includes, for example, multiple arrays of detection elements arranged along a single arc about the focal point of the X-ray tube 11 in a channel direction. The X-ray detector 12 has a structure that multiple detection element arrays are arranged in a slice direction (column or row direction), for example. Various types of the X-ray CT apparatus 1 are available, including a rotate/rotate-type (third generation CT) that the X-ray tube 1 and the X-ray detector 12 rotate together around the subject P, and a stationary/rotate-type (fourth generation CT) that a large number of X-ray detection elements are stationarily arranged in a ring form and the X-ray tube 11 alone rotates around the subject P. Any type is applicable to the present embodiment.

The X-ray detector 12 is exemplified by an indirect-conversion detector including a grid, a scintillator array, and an optical sensor array. The scintillator array includes multiple scintillators and each scintillator includes a scintillator crystal that outputs light having a quantity of photon corresponding to an amount of incident X-rays. The grid is disposed on the X-ray incident side of the scintillator array and includes an X-ray shield plate that functions to absorb scattered X-rays. The grid may be referred to as a collimator (one-dimensional collimator or two-dimensional collimator). The optical sensor array functions to convert an amount of light from the scintillators into an electric signal, and includes, for example, optical sensors such as photo multipliers (PMT). The X-ray detector 12 may be a direct-conversion detector including a semiconductor element that converts an incident X-ray into an electric signal. Alternatively, the X-ray detector 12 may be a photon counting X-ray detector. The X-ray detector 12 is an exemplary X-ray detector unit.

The rotational frame 13 is an annular frame that supports the X-ray tube 11 and the X-ray detector 12 in opposing positions to rotate the X-ray tube 11 and the X-ray detector 12 under the control of a control device 15 as later described. The rotational frame 13 further includes the X-ray high voltage apparatus 14 and the DAS 18 and supports them, in addition to the X-ray tube 11 and the X-ray detector 12. The rotational frame 13 is rotatably supported by a non-rotational part (e.g., a stationary frame, not illustrated in FIG. 1) of the gantry apparatus 10. The rotational mechanism includes a motor that generates rotative drive force and a bearing that transmits the rotative drive force to the rotational frame 13 to rotate, for example. The motor is disposed in, for example, the non-rotational part. The bearing is physically connected to the rotational frame 13 and the motor to rotate the rotational frame 13 in accordance with the rotative force of the motor.

The rotational frame 13 and the non-rotational part are each equipped with non-contact or contact communication circuitry which allows the units supported by the rotational frame 13 to communicate with the non-rotational part or external devices of the gantry apparatus 10. In the case of adopting a non-contact optical communication method, for instance, detection data generated by the DAS 18 is transmitted by optical communication from a transmitter with light emitting diodes (LED) included in the rotational frame 13 to a receiver with photodiodes included in the non-rotational part of the gantry apparatus 10, and then transferred by a transmitter from the non-rotational part to the console device 40. Other examples of adoptable communication methods include a non-contact data transfer method such as capacitive-coupling or via radio waves and a contact data transfer method using a slip ring and an electrode brush. The rotational frame 13 is an exemplary rotational unit.

The X-ray high voltage apparatus 14 includes a high voltage generator and an X-ray control device. The high voltage generator includes electric circuitry such as a transformer and a rectifier and functions to generate a high voltage to be applied to the X-ray tube 11 and a filament current to be supplied to the X-ray tube 11. The X-ray control device controls the output voltage in accordance with the X-rays emitted from the X-ray tube 11. The high-voltage generator may be of a transformer type or of an inverter type. Further, the X-ray high-voltage apparatus 14 may be disposed in the rotational frame 13 or in the stationary frame of the gantry apparatus 10. The X-ray high voltage apparatus 14 is an exemplary X-ray high voltage unit.

The control device 15 includes memory and processing circuitry including a central processing unit (CPU), and a driving mechanism such as a motor and an actuator. In response to receipt of an input signal from an input interface attached to the console device 40 or the gantry apparatus 10, the processing circuitry functions to control the operation of the gantry apparatus 10 and the couch apparatus 30. As an example, the control device 15 controls the rotation of the rotational frame 13, the tilting of the gantry apparatus 10, and the operation of the couch apparatus 30 and a tabletop 33 in response to receipt of input signals. The control device 15 causes the gantry apparatus 10 to tilt by rotating the rotational frame 13 about an axis parallel to the X axis direction according to tilt-angle information input to the input interface attached to the console device 40. The control device 15 may be included in the gantry apparatus 10 or in the console device 40. Various programs to be executed by the control device 15 may be directly embedded in a processor circuit of the control device 15, in place of being stored in the memory. The control device 15 is an exemplary control unit.

The wedge 16 is a filter for adjusting the amount of X-rays emitted from the X-ray tube 11. Specifically, the wedge 16 serves to allow the X-rays emitted from the X-ray tube 11 to transmit therethrough for attenuation, so that the subject P is irradiated with the X-rays from the X-ray tube 11 in a predefined distribution. The wedge 16 is formed of aluminum and has a given target angle and a given thickness. Examples of the wedge 16 include a wedge filter and a bow-tie filter.

The collimator 17 includes a combination of lead plates forming slits, to converge the X-rays having transmitted the wedge 16 in an irradiation range, for example. The collimator 17 may be referred to as an X-ray aperture.

The DAS 18 includes an amplifier that amplifies the electric signals output from the respective X-ray detection elements of the X-ray detector 12, and an A/D converter that converts the electric signals into digital signals. Thus, the DAS 18 generates detection data. The DAS 18 transfers the detection data to processing circuitry 44. The detection data may be referred to as pure raw data. The DAS 18 is an exemplary data acquirer unit.

The couch apparatus 30 serves to allow the subject P to be scanned to lie down thereon, and move the subject P. The couch apparatus 30 includes a base 31, a couch driver 32, a tabletop 33, and a support frame 34. The base 31 serves as a casing that movably supports the support frame 34 in a vertical direction. The couch driver 32 is a motor or an actuator that moves the tabletop 33, on which the subject P is laid, along the long axis of the tabletop 33. The tabletop 33 is a plate on which the subject P is laid, and is placed on the top surface of the support frame 34. The couch driver 32 may move the support frame 34 along the long axis of the tabletop 33, in addition to the tabletop 33.

The console device 40 includes a memory 41, a display 42, an input interface 43, and processing circuitry 44. The processing circuitry 44, the memory 41, the display 42, and the input interface 43 perform data communications with one another via, for example, a bus. Although the console device 40 and the gantry apparatus 10 are separately provided herein, the gantry apparatus 10 may include the console device 40 or part of the elements of the console device 40.

The memory 41 is implemented by, for example, a semiconductor memory element as a random access memory (RAM) or a flash memory, a hard disk, an optical disk, or a solid state drive (SSD). The memory 41 stores therein detection data output from the DAS 18, projection data generated by a preprocessing function 442, reconstructed medical image data by a reconstruction function 443, image data subjected to image processing by an image processing function 444, and imaging conditions for scanning of the subject P, for example. The medical image data is exemplified by three-dimensional CT image data and also referred to as reconstructed image data or volume data. The projection data and data before preprocessed by the preprocessing function 442 (i.e., detection data or pure raw data) are collectively referred to as raw data. That is, raw data can be pure raw data or projection data. The memory 41 further stores therein programs for executing a system control function 441, the preprocessing function 442, the reconstruction function 443, the image processing function 444, a determination function 445, and an adding function 446 to be implemented by the processing circuitry 44. The memory 41 is an exemplary storage unit.

The display 42 serves to display various kinds of information. For example, the display 42 outputs medical images (CT images) generated by the processing circuitry 44 and a graphical user interface (GUI) that allows the operator to perform various operational inputs as to image condition setting, reconstruction retry, and else. Examples of the display 42 include a liquid crystal display (LCD), a cathode ray tube (CRT) display, an organic electroluminescence display (OELD), a plasma display, or any other display when appropriate. Alternatively, the display 42 may be included in the gantry apparatus 10. As an example, the display 42 may be a desktop type or may include a tablet terminal wirelessly communicable with the console device 40 itself. The display 42 is an exemplary display unit.

The input interface 43 serves to receive various operational inputs from the operator to convert the operational inputs into electrical signals and output the electrical signals to the processing circuitry 44. As an example, the input interface 43 receives, from the operator, an imaging condition for acquiring projection data, a reconstruction condition for reconstructing CT image data, an image processing condition for post-processing CT image data, and else. The post-processing may be performed by either the console device 40 or an external workstation or by both of the console device 40 and an external workstation concurrently. Herein, the post-processing is defined as a concept for signifying processing with respect to images reconstructed by the reconstruction function 443. The post-processing includes a multi planar reconstruction (MPR) display of medical images and/or volume data rendering, by way of example. Examples of the input interface 43 include a mouse, a keyboard, a trackball, a switch, a button, a joystick, a touchpad, and a touch panel display, as appropriate.

In the present embodiment the input interface 43 is not limited to the one including a physical operational component such as a mouse, a keyboard, a trackball, a switch, a button, a joystick, a touchpad, and a touch panel display. Other examples of the input interface 43 include electrical-signal processing circuitry that receives an electrical signal corresponding to an operational input from an external input device separated from the apparatus to output the electrical signal to the processing circuitry 44.

Alternatively, the input interface 43 may be included in the gantry apparatus 10. For another example, the input interface 43 may include a tablet terminal wirelessly communicable with the console device 40 itself. The input interface 43 is an exemplary input unit.

The processing circuitry 44 serves to control the X-ray CT apparatus 1 as a whole in accordance with electric signals representing operational inputs as output from the input interface 43, for example. The processing circuitry 44 includes, for example, hardware resources including a processor such as a CPU, an MPU, or a graphics processing unit (GPU) and a memory such as a ROM or a RAM. The processing circuitry 44 includes a processor that loads and executes programs on the memory, to implement the system control function 441, the preprocessing function 442, the reconstruction function 443, the image processing function 444, the determination function 445, and the adding function 446. The respective functions 441 to 446 may not be implemented by a single processing circuit. The processing circuitry 44 can be constituted of a combination of multiple independent processors, so that the processors can individually execute the programs to implement the respective functions 441 to 446.

The system control function 441 serves to control the respective functions of the processing circuitry 44 in response to receipt of operational inputs from the operator via the input interface 43. The system control function 441 reads and loads control programs from the memory 41 onto the memory inside the processing circuitry 44 to control the respective units of the X-ray CT apparatus 1 by the control programs. The system control function 441 is an exemplary control unit.

The preprocessing function 442 serves to subject the detection data output from the DAS 18 to preprocessing including, for example, logarithm conversion, offset correction, sensitivity correction among the channels, and beam hardening correction, to generate data. Data before being preprocessed is referred to as pure raw data while data after being preprocessed is referred to as projection data, as described above. The preprocessing function 442 is an exemplary preprocessing unit.

The reconstruction function 443 serves to perform reconstruction processing to raw data generated by scanning the subject P to reconstruct a medical image. Specifically, the reconstruction function 443 generates medical image data by performing reconstruction processing to the projection data generated by the preprocessing function 442 by filtered back projection (FBP), for example. The reconstruction processing includes various kinds of processing such as various corrections as scattering correction and beam hardening correction, and application of mathematical reconstruction functions to the reconstruction conditions. The reconstruction function 443 stores reconstructed medical image data in the memory 41. The reconstruction function 443 is an exemplary reconstruction unit.

The image processing function 444 serves to convert medical image data into planar image data of any view or three-dimensional image data by a known method, in accordance with operational inputs received from the operator via the input interface 43. The reconstruction function 443 may directly generate three-dimensional image data. The image processing function 444 is an exemplary image processing unit.

The determination function 445 serves to determine a posture of the subject P at the time of a scan according to an imaging condition reflecting an examination order for the scan. The determination function 445 may determine the imaging condition with reference to an examination order output from a radiology information system (hereinafter, RIS) or a hospital information system (hereinafter, HIS). As an example, if the examination order specifies the posture of the subject P in a scan, the determination function 445 determines the imaging condition based on the posture specified in the examination order. The posture of the subject P refers to, for example, the body position of the subject P in a scan and includes, but is not limited to, upright, decubitus, and seated positions. The posture of the subject P can be an oblique body position tilting from the horizontal plane of the tabletop 33 (hereinafter, oblique position), for example. The imaging condition is also referred to as an imaging protocol and defines, for example, settings of each scan including radiation dose, tube voltage, tube current, scan speed, slice thickness, and imaging mode as well as a phase representing an order of imaging with respect to a pre-scan for setting an imaging range and a main scan such as a helical scan and a step and shoot scan. The imaging modes correspond to various scanning modes as a helical scan (H), a step and shoot scan (S & S), a scan and view (S & V), and a dynamic scan. The imaging condition may include posture information included in the examination order. In accordance with an operator's instruction via the input interface 43, the determination function 445 may determine the imaging condition and/or the posture. The determination function 445 is an exemplary determiner unit. In addition the processing circuitry 44 may infer the posture of the subject P at the time of a scan by collating between combinations of various posture items set in the imaging condition and a table containing postures corresponding to the combinations.

The adding function 446 serves to add information as to the posture determined by the determination function 445 (hereinafter, posture-related information) to the raw data and the medical image. The posture-related information refers to, for example, strings representing the body position or posture of the subject P in a scan, an icon (hereinafter, posture icon) schematically representing the strings, angular information of decubitus, upright, and oblique positions with respect to the horizontal plane, and gravity information indicating the direction of gravity. The adding function 446 refers to the posture-related information for transmitting a medical image to a server of picture archiving and communication systems (hereinafter, PACS) according to the posture or for searching for a medical image according to the posture. The adding function 446 is an exemplary adder unit.

With reference to FIG. 2 to FIG. 11, a posture display process of the X-ray CT apparatus 1 as configured above in the present embodiment will be described. The posture display process refers to a process of displaying a medical image of the subject P generated by scanning, in association with the posture-related information of the subject P during the scanning. Prior to execution of the posture display process, the memory 41 stores the posture-related information.

Figure 2:
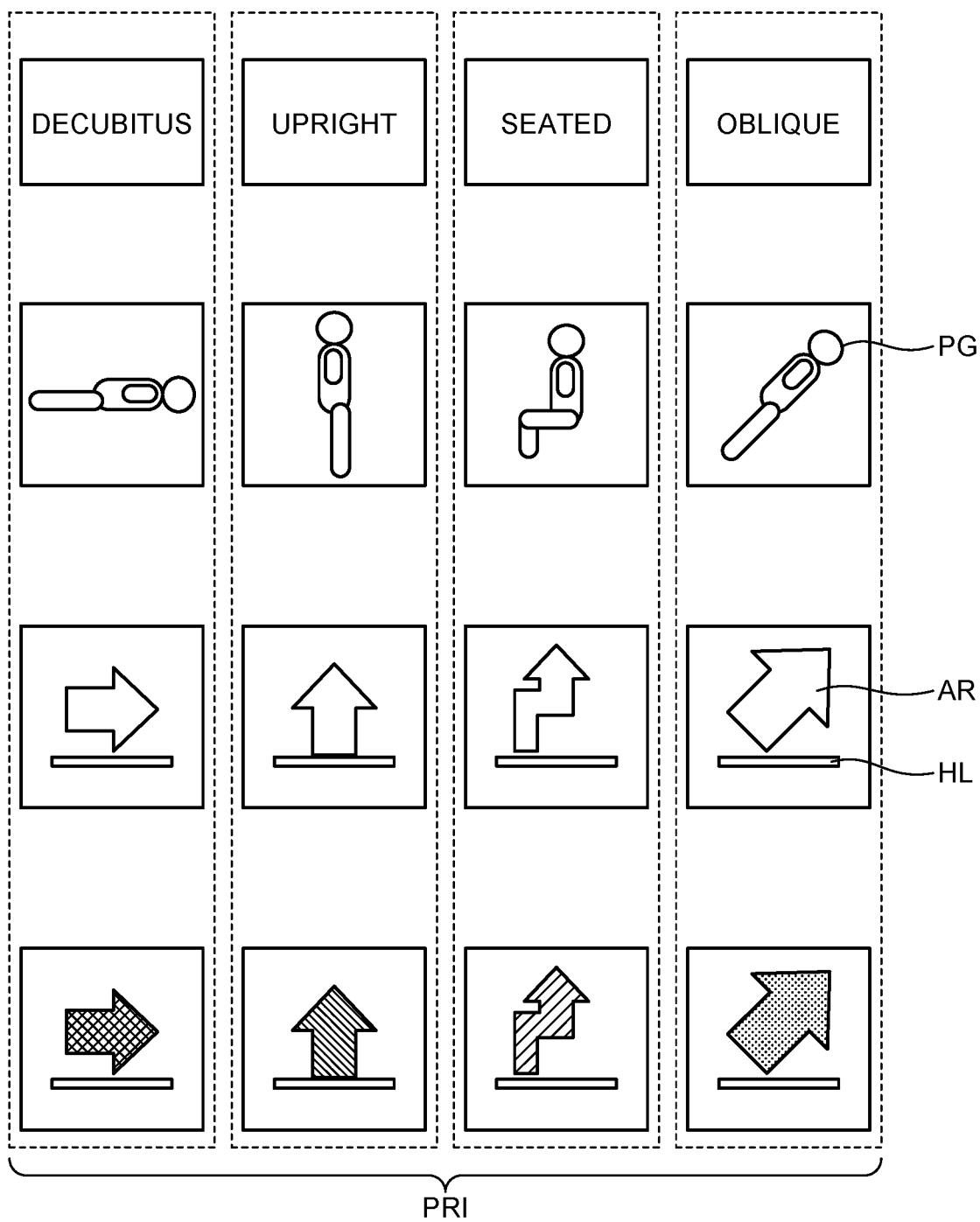
FIG. 2 illustrates exemplary posture-related information according to the first embodiment.

FIG. 2 illustrates posture-related information PRI by way of example. As illustrated in FIG. 2, the memory 41 stores strings and posture icons as a schematic and visual representation of the postures or body positions of the subject P at the time of a scan. The posture icons schematically and visually representing the postures or body positions of the subject P at the time of a scan may be represented in different hues (by different hatchings in FIG. 2) depending on the posture or body position of the subject P. As an example, a decubitus position is depicted in green, an upright position is depicted in red, and a seated position is depicted in yellow. In FIG. 2 arrows AR point to the head of the subject P and horizontal lines HL below the arrows represent a floor. In place of the horizontal line HL representing a floor, the posture icon may include a symbol representing a vertical direction, together with an arrow indicating the posture of the subject P. In addition, visual symbols PG each schematically and visually represent a human body to indicate the posture of the subject P and may additionally include the horizontal line HL representing a floor or the symbol representing a vertical direction. The posture-related information PRI is not limited to the examples illustrated in FIG. 2, and may be represented in various forms with omissions, replacements, modifications, and combinations as appropriate, in accordance with the posture of the subject P.

Figure 3:
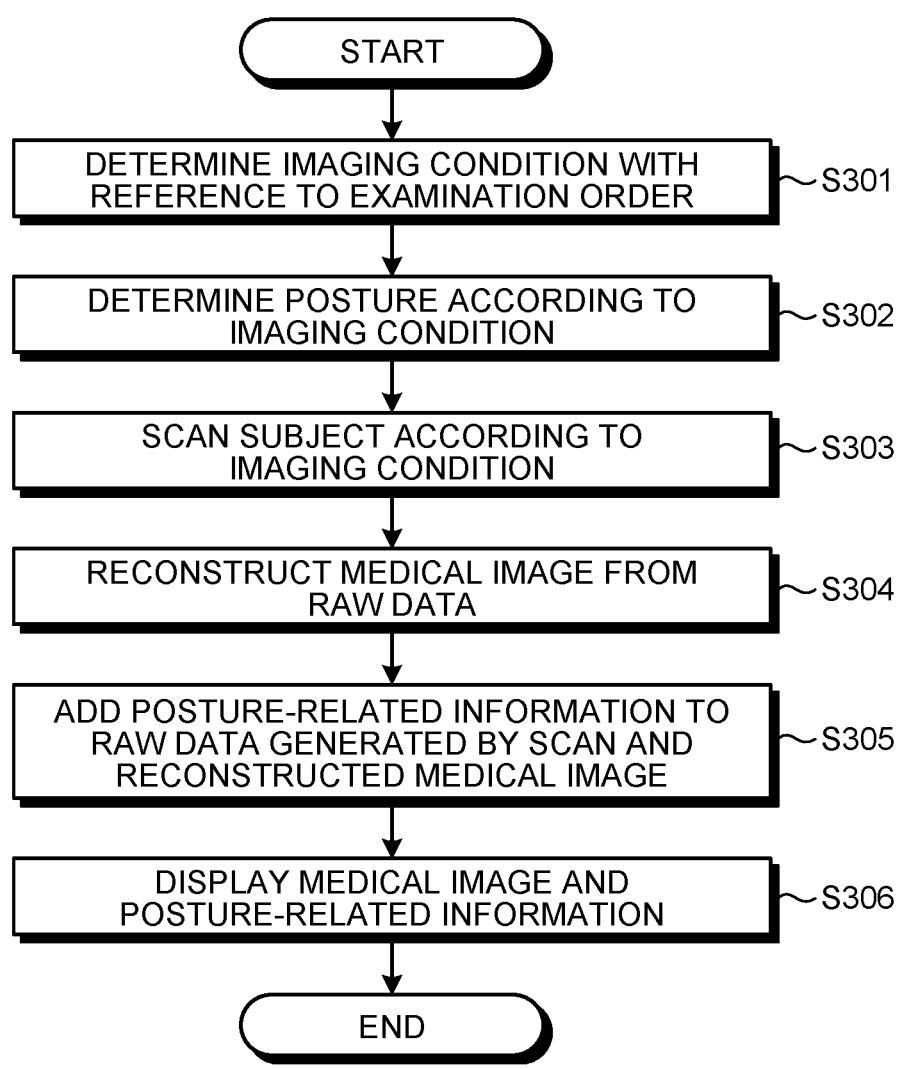
FIG. 3 is a flowchart illustrating a posture display process in the first embodiment by way of example.

FIG. 3 is a flowchart illustrating the posture display process by way of example.

Posture Display Process

Step S301

The determination function 445 determines an imaging condition for the subject P with reference to an examination order output from the RIS or the HIS. Specifically, the determination function 445 determines an imaging condition with reference to an examination order, following an operator's instruction via the input interface 43. To determine the imaging condition, the posture or body position of the subject P in a scan may be input according to an operator's instruction via the input interface 43. The examination order may specify the posture or body position of the subject P at the time of a scan. In such a case the determination function 445 may determine the imaging condition according to the posture or body position specified in the examination order. The display 42 then displays the determined imaging condition and posture information included in the examination order.

Step S302

The determination function 445 determines the posture of the subject P at the time of the scan according to the imaging condition for the scan as determined in step S301. Specifically, when the imaging condition indicates a scan in an upright state (hereinafter, referred to as upright scanning), the determination function 445 determines the posture of the subject P as upright. When the imaging condition indicates a scan in a decubitus state (hereinafter, referred to as decubitus scanning), the determination function 445 determines the posture of the subject P as decubitus. Further, when the imaging condition indicates a scan in a seated state (hereinafter, referred to as seated scanning), the determination function 445 determines the posture of the subject P as seated. When the imaging condition indicates a scan in an oblique state (hereinafter, referred to as oblique scanning), the determination function 445 determines the posture of the subject P as oblique.

The determination function 445 may detect the posture or body position from the examination order through a language analysis of the examination order, to determine the posture of the subject P at the time of the scan. In addition the determination function 445 may automatically determine the posture of the subject P based on outputs of external devices such as various kinds of cameras installed in the examination room in which the X-ray CT apparatus 1 is installed, mechanical angle detection with an acceleration sensor included in the gantry apparatus 10, or internal information as to imaging of the subject P for positioning (positioning scan), for instance. The display 42 displays the imaging condition along with the posture information.

FIG. 4 illustrates exemplary posture-related information PRI on display together with a scan-plan list PL. A scan plan contains, for example, a row of items (e.g., tube voltage 802, tube current 803, scan time 804) of the imaging condition for a scan with identification number 801 and corresponds to a row of the list PL in FIG. 4. In the item "body-position information" in each row of the list PL, the posture icon representing the posture-related information PRI is displayed.

As illustrated in FIG. 4, an instruction for changing a posture icon RI may be input via the input interface 43. Change of the posture icon RI is instructed by, for example, clicking the posture icon RI. In response to an instruction for changing the posture to another posture relative to the posture information on display together with the imaging condition, the determination function 445 determines another imaging condition for another posture. That is, in response to a change of the posture icon to another posture icon, the determination function 445 changes the imaging condition to another imaging condition associated with another posture icon, in accordance with another posture icon and the examination order. The display 42 then displays another imaging condition and another posture information in question (another posture icon).

Step S303

The system control function 441 scans the subject P according to the imaging condition. The system control function 441 stores raw data generated by scanning in the memory 41.

Step S304

The reconstruction function 443 reconstructs the medical image from the raw data. The reconstruction function 443 stores the reconstructed medical image in the memory 41.

Step S305

The adding function 446 adds posture-related information to the raw data generated by scanning in step S303 and to the medical image reconstructed in step S304. Specifically, the adding function 446 reads, from the memory 41, the posture-related information of the posture determined by the determination function 445, to add the posture-related information to the raw data and the medical image.

Step S306

The display 42 displays the medical image in association with the posture-related information PRI. As an example, by the posture-related information PRI, the display 42 displays the medical image such that types of posture, i.e., decubitus, upright, seated, oblique, and other postures, are identifiable. In the case of using the gantry apparatus 10 changeable in position and orientation, i.e., the X-ray CT apparatus 1 capable of scanning the subject in both the upright position and the decubitus position (hereinafter, referred to as universal CT apparatus), the display 42 may display angular information such as the angle of rotation of the gantry apparatus 10 as the posture-related information.

Specifically, the display 42 displays at least one of: the medical image and upright-position information contained in the posture-related information PRI when the posture determined is upright; the medical image and decubitus-position information contained in the posture-related information PRI when the posture determined is decubitus; and the medical image and seated-position information contained in the posture-related information PRI when the posture determined is seated. As an example, the display 42 does not display the posture-related information when the subject has been scanned in a normal decubitus position, and displays the posture-related information when the subject has been scanned in an upright position or a seated position.

In the case of displaying information indicating the direction of gravity as the posture-related information, the information indicating the direction of gravity may be considered as substantially equivalent to the posture information of the subject P. It is, however, impossible to distinguish the upright position and the seated position based on the direction-of-gravity information. In this regard, under a situation that the state of the subject changes between the upright position and the seated position, displaying not the direction-of-gravity information but the posture-related information PRI illustrated in FIG. 2 has significance in the universal CT apparatus, for example. In the following, examples of the display of the posture-related information PRI will be described with reference to FIG. 5 to FIG. 11.

Figure 5:
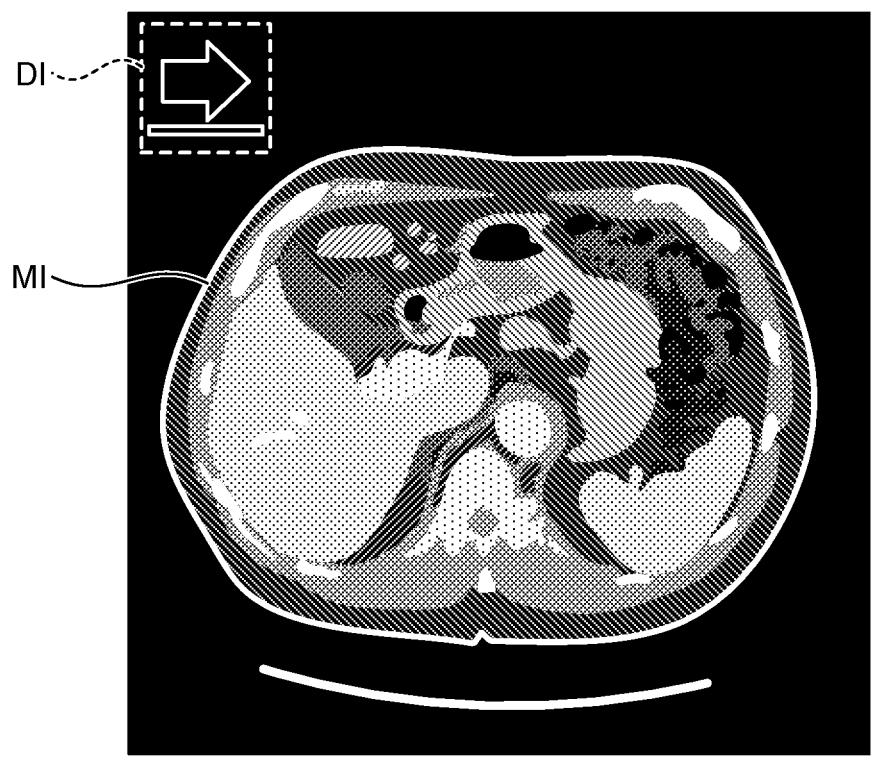
FIG. 5 illustrates a display of a medical image and posture-related information as to a decubitus position on a display in the first embodiment by way of example.

FIG. 5 depicts a medical image MI and posture-related information DI as to a decubitus position displayed on the display 42, by way of example. The medical image MI is generated by decubitus scanning, and thus the display 42 displays the posture-related information DI indicating a decubitus position together with the medical image MI, as illustrated in FIG. 5.

Figure 6:
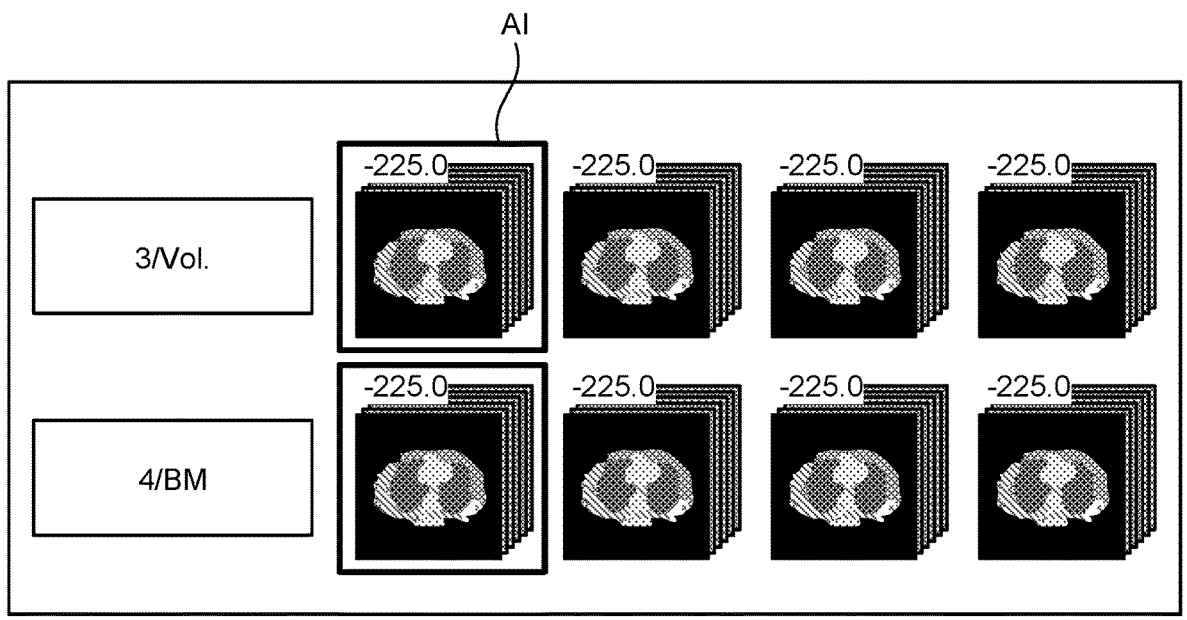
FIG. 6 illustrates an exemplary display of a plurality of medical images generated by decubitus scanning, which are schematically arranged in units of series or volume to be selectable by the operator, in the first embodiment.

FIG. 6 illustrates an exemplary display of multiple medical images generated by decubitus scanning, which are schematically arranged in units of series or volume to be selectable by the operator. As illustrated in FIG. 6, typical medical images AI serving as the posture-related information are displayed in an axial view so as to allow the operator to easily visually recognize that the subject has been scanned in a decubitus position.

Figure 7:
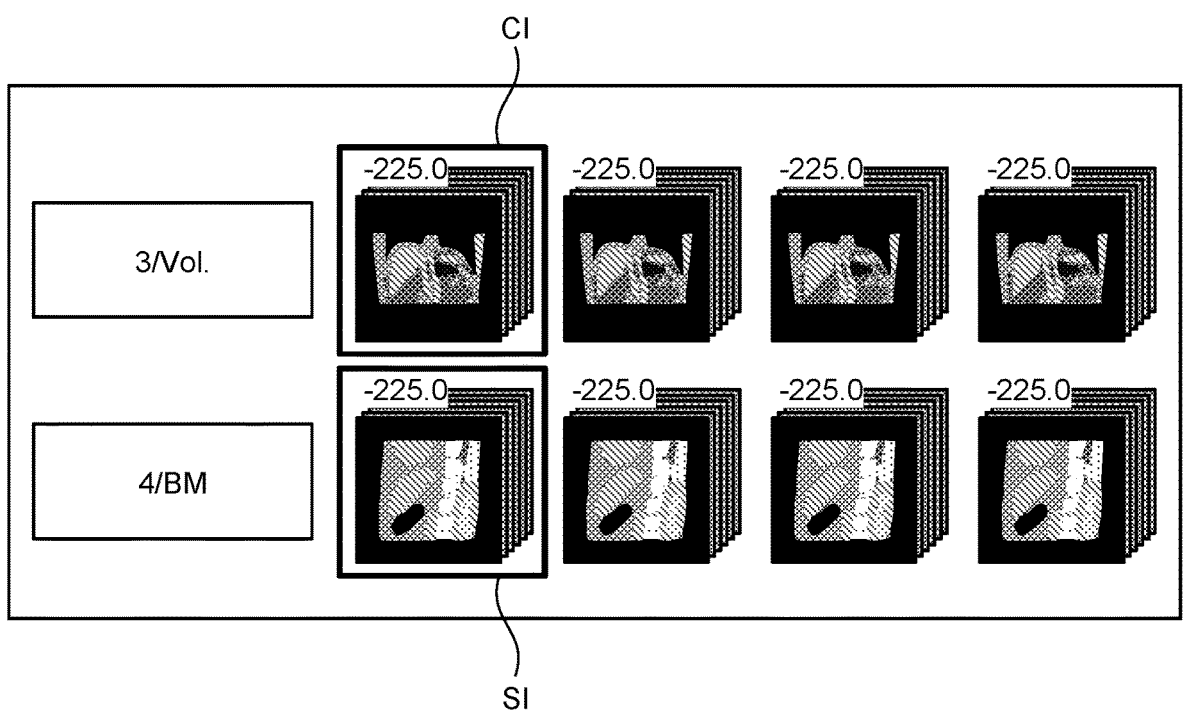
FIG. 7 illustrates an exemplary display of a plurality of medical images generated by upright scanning, which are schematically arranged in units of series or volume to be selectable by the operator, in the first embodiment.

FIG. 7 illustrates an exemplary display of multiple medical images generated by upright scanning, which are schematically arranged in units of series or volume to be selectable by the operator. As illustrated in FIG. 7, typical medical images CI serving as the posture-related information are displayed in a coronal view to allow the operator to easily visually recognize that the subject has been scanned in an upright position. Further, as illustrated in FIG. 7, typical medical images SI serving as the posture-related information are displayed in a sagittal view to allow the operator to easily visually recognize that the subject has been scanned in an upright position. The typical images that allow identification of upright scanning can be in either of a coronal view and a sagittal view.

Figure 8:
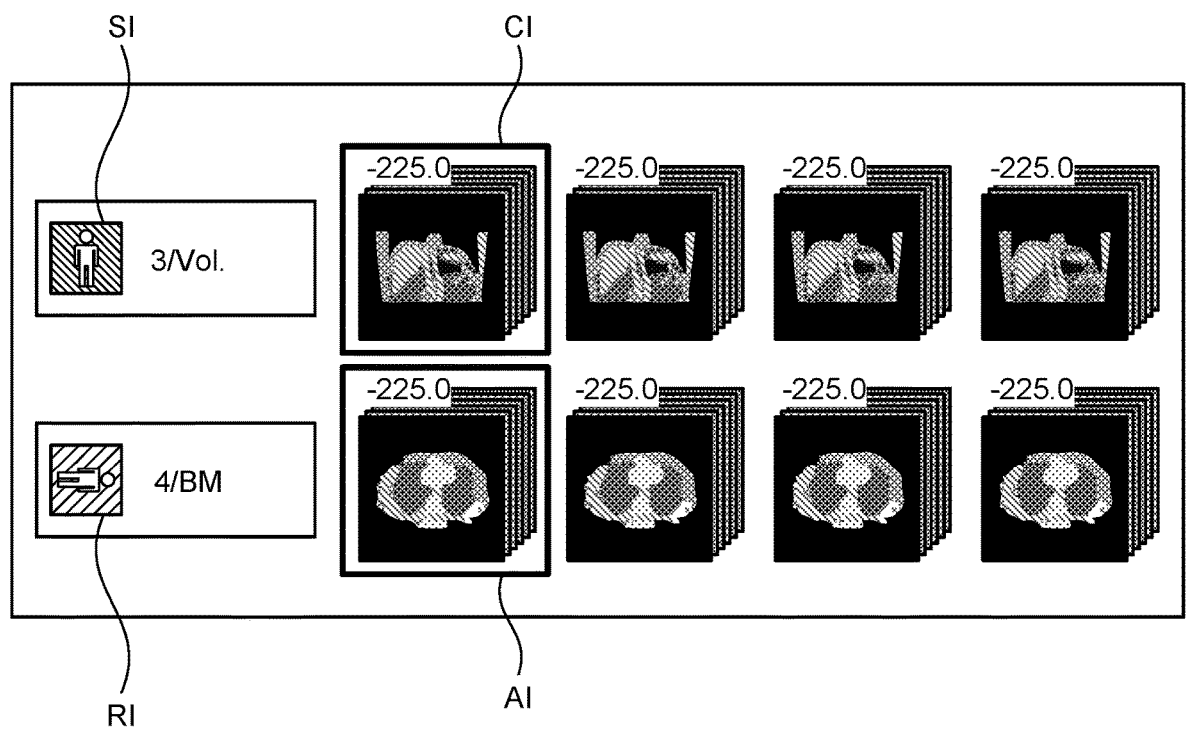
FIG. 8 illustrates an exemplary display of a plurality of medical images generated by decubitus scanning and upright scanning, which are schematically arranged in units of series or volume to be selectable by the operator, in the first embodiment.

FIG. 8 illustrates an exemplary display of multiple medical images generated by decubitus scanning and upright scanning, which are schematically arranged in units of series or volume to be selectable by the operator. As illustrated in FIG. 8, typical medical images CI serving as the posture-related information are displayed in a coronal view to allow the operator to easily visually recognize that the subject has been scanned in an upright position. Further, as illustrated in FIG. 8, typical medical images AI serving as the posture-related information are displayed in an axial view to allow the operator to easily visually recognize that the subject has been scanned in a decubitus position. Additionally, scan icons (3/Vol. and 4/BM) including posture icons are displayed along with the typical medical images associated with the scans. The posture icons indicate posture-related information as to the respective scans. In FIG. 8 a posture icon RI represents decubitus scanning as in FIG. 2. In FIG. 8 a posture icon SI represents upright scanning as in FIG. 2.

Figure 9:
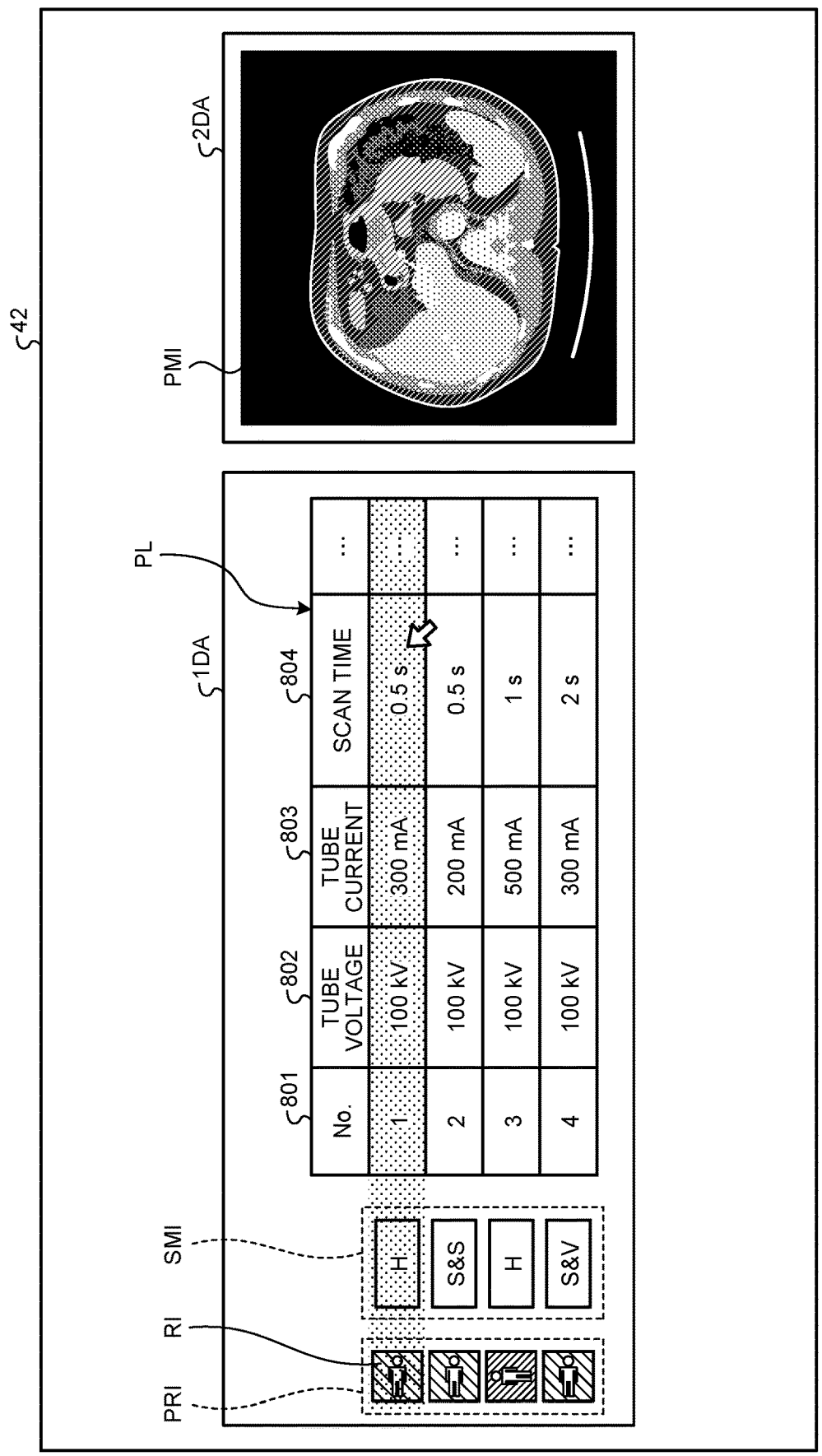
FIG. 9 illustrates another exemplary posture-related information and a scan-plan list on display in the first embodiment.

FIG. 9 illustrates another exemplary posture-related information PRI on display together with the scan-plan list PL. As illustrated in FIG. 9, the display 42 displays, adjacent to the scan-plan list PL, icons SMI (H, S&S, S&V) representing imaging modes with individual identification numbers 801. For example, the display 42 displays, in a first display region 1DA, a list containing rows of imaging conditions and the icons SMI representing imaging modes in scans for individual scans. In addition the display 42 highlights a scan plan selected by the operator on the list PL. The display 42 then displays a medical image associated with the selected scan plan in a second display region 2DA. The display 42 also displays posture-related information PRI associated with the scan in the first display region 1DA adjacent to the icons SMI representing the imaging modes.

In FIG. 9 the scan plan with identification No. 1 is selected and highlighted, and a typical medical image PMI captured according to the scan plan with identification No. 1 is displayed in the second display region 2DA. As illustrated in FIG. 9, the imaging mode set in the scan plan with identification No. 1 is helical scanning so that the scan-plan icon, i.e., the icon H representing the imaging mode is displayed next to the scan plan with identification No. 1 in the first display region 1DA. The display 42 also displays posture-related information RI associated with the selected scan in the first display region 1DA next to the icon H. The display 42 may display both the medical image PMI and the posture-related information RI in the second display region 2DA.

Figure 10:
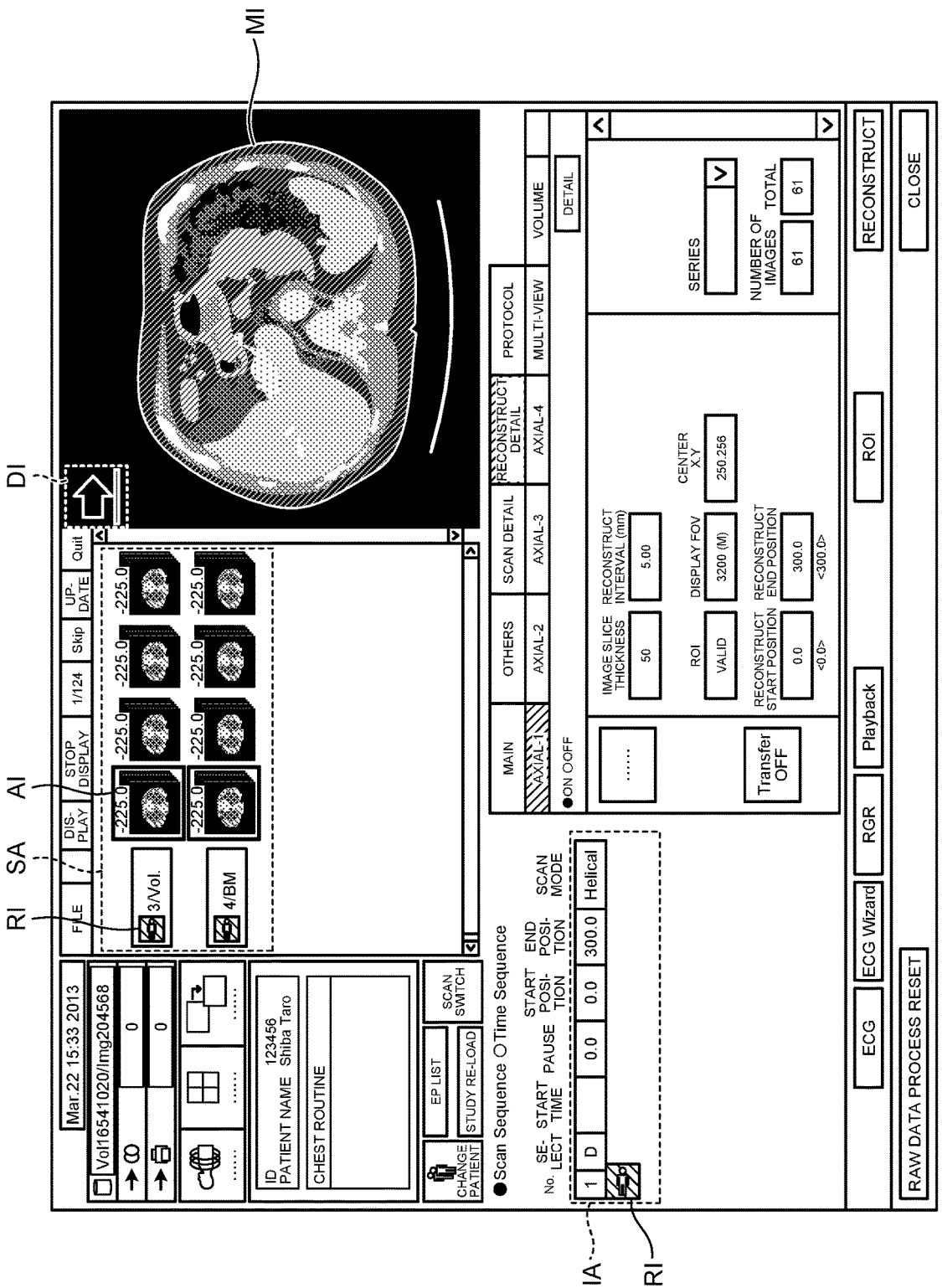
FIG. 10 illustrates an exemplary display mode which allows the operator to input a reconstruction condition different from the one for a reconstructed medical image concerned in the first embodiment.

FIG. 10 illustrates an exemplary display mode which allows an input of a different reconstruction condition from the reconstruction condition for the reconstructed medical image concerned. The display mode corresponds to a reconstruction-retry display screen for reconstructing a medical image again under a different reconstruction condition. In response to an input of a reconstruction retry instruction from the operator via the input interface 43, the display 42 displays the display mode as illustrated in FIG. 10. As illustrated in FIG. 10, the display 42 displays a reconstructed medical image MI and posture-related information DI indicating a decubitus position on a reconstruction-condition input screen in the reconstruction retry. The display 42 displays the posture-related information DI indicating a decubitus position in a reconstruction-condition input region IA and an image select region SA, as shown in FIG. 10.

The image processing function 444 performs conversion between medical images associated with different postures. For example, the image processing function 444 converts the reconstructed medical image in step S304 to a posture transformed image associated with another posture different from the one determined in step S302. The image conversion is, for example, implemented by multiple image filters generated by a trained deep convolutional neural network (DCNN) using pairs of upright-position and seated-position images, upright-position and decubitus-position images, and seated-position and decubitus-position images. In this regard, an organ appears in different positions (hereinafter, referred to as organ droop) on the medical image depending on the posture and body position of the subject P while being scanned. Due to the gravity, for example, an organ appears in a lower position on a reconstructed medical image generated by upright scanning (hereinafter, referred to as upright image) than on a reconstructed medical image generated by decubitus scanning (hereinafter, referred to as decubitus image). The multiple image filters correspond to filters that can reproduce or reduce such an organ droop.

The image processing function 444 inputs the medical images to the image filters to thereby mutually convert between the upright image and the decubitus image, between a reconstructed medical image as a result of seated scanning (hereinafter, referred to as seated image) and the decubitus image, and between the upright image and the seated image. As an example, the image processing function 444 generates a posture transformed image corresponding to the upright image by inputting the decubitus image reconstructed in step S304 to the image filter serving to convert the decubitus image to the upright image. The display 42 displays the posture transformed image, information indicating that the posture transformed image has been converted from the medical image (hereinafter, referred to as conversion information), and another posture information (posture-related information) together.

Figure 11:
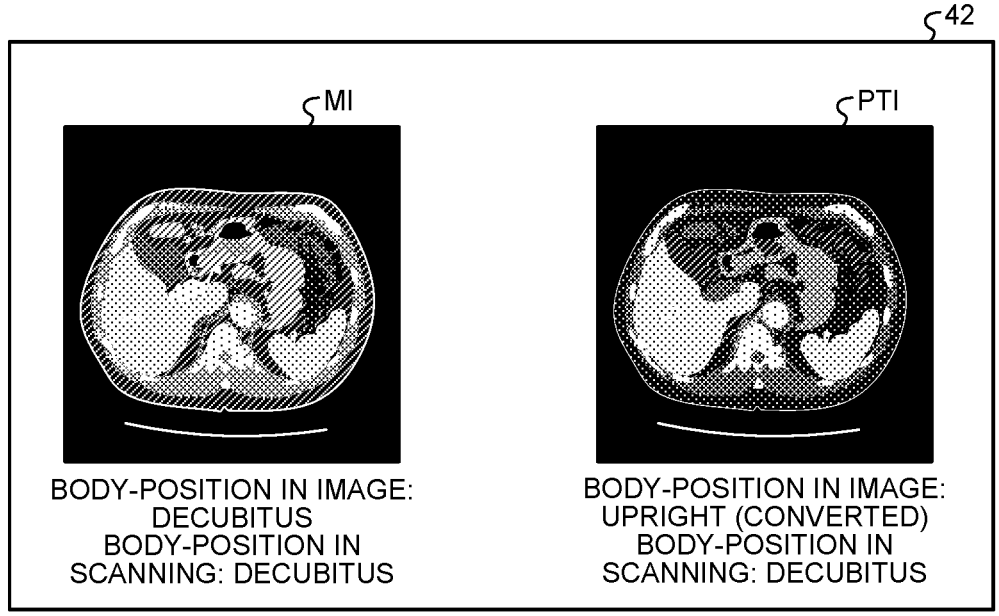
FIG. 11 illustrates a display of exemplary conversion information and posture-related information together with a medical image and a posture transformed image in the first embodiment.

FIG. 11 illustrates exemplary conversion information and posture-related information on display together with a medical image MI and a posture transformed image PTI. In FIG. 11 "body position in scanning" represents a body position of the subject P while being scanned and "body position in image" represents a body position in the medical image and the posture transformed image on display. The body position in scanning and the body position in image correspond to the posture-related information. In addition the string "converted" in FIG. 11 represents information that the posture transformed image PTI has been converted from the medical image MI.

In accordance with an operator's instruction via the input interface 43, the medical image displayed in step S306 is transmitted to, for example, the PACS server. The medical image has the posture-related information added thereto, which thus enables the operator to transmit the medical image to the PACS server according to the posture or body position of the subject P at the time of the scan. Further, following an operator's instruction via the input interface 43, the system control function 441 searches for a medical image linked with the posture-related information, according to the posture or body position of the subject P at the time of the scan. The display 42 displays the medical image found through the search together with the posture-related information and the imaging condition. This makes it possible for the operator to easily refer to the imaging condition according to the posture or body position of the subject P at the time of the scan, for example. Thus, the X-ray CT apparatus 1 of the present embodiment can improve efficiency and throughput in terms of the examination of the subject.

The X-ray CT apparatus 1 of the first embodiment as described above reconstructs a medical image by performing reconstruction processing to raw data generated by a scan of the subject P, determines a posture of the subject P at the time of the scan, according to an imaging condition for the scan, and displays the medical image in association with information on the posture. As an example, the X-ray CT apparatus 1 displays the medical image in a manner that the type of the posture (i.e., decubitus, upright, seated, oblique, and other postures) is identifiable. Specifically, the X-ray CT apparatus 1 displays at least one of: the medical image and upright-position information when the posture is upright; the medical image and decubitus-position information when the posture is decubitus; and the medical image and seated-position information when the posture is seated. Owing to such features, in displaying a reconstructed medical image, the X-ray CT apparatus 1 enables the operator to easily determine in what posture the subject has been scanned to capture the medical image, without accessing detailed information (e.g., property) on the medical image. Thereby, the operator can transfer the medical image to the PACS server according to the posture of the subject P at the time of the scan, and can easily know the posture or body position of the subject P in the medical image at the time of a radiographic diagnosis, for example. Thus, the X-ray CT apparatus 1 can improve efficiency in terms of examination and radiographic diagnosis.

Further, the X-ray CT apparatus 1 of the first embodiment displays, in the first display region, the list containing rows of imaging conditions and icons representing imaging modes in scans for individual scans, displays a medical image associated with a scan selected from the list in the second display region, and displays information as to the posture associated with the scan in the first display region adjacent to the icon. In addition the X-ray CT apparatus 1 displays the medical image and the information as to the posture in the display mode which allows input of reconstruction conditions different from the one for the medical image in question. Owing to such features, the X-ray CT apparatus 1 enables the operator to easily, with no confusion, determine in what posture the subject P has been scanned to capture the medical image, without accessing detailed information as to the medical image in the scan-plan list PL on display or on the reconstruction-retry input screen. Thereby, the X-ray CT apparatus 1 can improve efficiency in terms of examination and/or post-processing including reconstruction retry.

If the examination order for the subject P specifies a posture, the X-ray CT apparatus 1 of the first embodiment determines an imaging condition for the posture and displays the determined imaging condition and information as to the posture included in the examination order. In response to receipt of an instruction for changing the posture to another posture with respect to the information as to the posture displayed together with the imaging condition, the X-ray CT apparatus 1 changes the imaging condition to another imaging condition associated with another posture, and displays another imaging condition and information as to another posture together. Owing to such features, the X-ray CT apparatus 1 enables the operator to readily know, prior to scanning, the posture of the subject P at the time of a scan, to change the imaging condition at ease. There may be a case, for example, that scanning of the subject P in an upright position is unfeasible because of old age, injuries, fatigue, or else, in spite of receipt of an examination order specifying a scan of the subject P in an upright position. In such a case the operator can easily change the imaging condition to the one for scanning the subject P in a seated or decubitus position. Likewise, in spite of receipt of an examination order specifying a scan of the subject P in a decubitus position, the subject P may be in a good condition to be able to undergo scanning in a simple upright position. In such a case the operator can easily change the imaging condition. Because of such features, the X-ray CT apparatus 1 can improve examination efficiency.

The X-ray CT apparatus 1 of the first embodiment converts a medical image to a posture transformed image associated with another posture different from the posture concerned, and displays the posture transformed image together with information as to another posture and information representing that the posture transformed image has been converted from the medical image. Thereby, in displaying a reconstructed medical image, the X-ray CT apparatus 1 enables the operator to easily determine the posture and body position of the subject P associated with the medical image on display without accessing detailed information (e.g., property representing setting and/or attribute information) of the medical image. Thus, the X-ray CT apparatus 1 can transfer the medical image to the PACS server, for example, according to the posture of the subject P, resulting in improving examination efficiency.

Further, the X-ray CT apparatus 1 of the first embodiment adds information as to the posture to the raw data and the medical image. Thereby, the X-ray CT apparatus 1 can readily search for the medical image and/or transfer the medical image according to the information as to the posture such as upright, decubitus, or seated, resulting in improving examination efficiency.

Second Embodiment

The features of a second embodiment are in that a medical image display apparatus implements a process of adding posture-related information to previous medical images, for example. The medical image display apparatus is also capable of implementing a posture display process.

Figure 12:
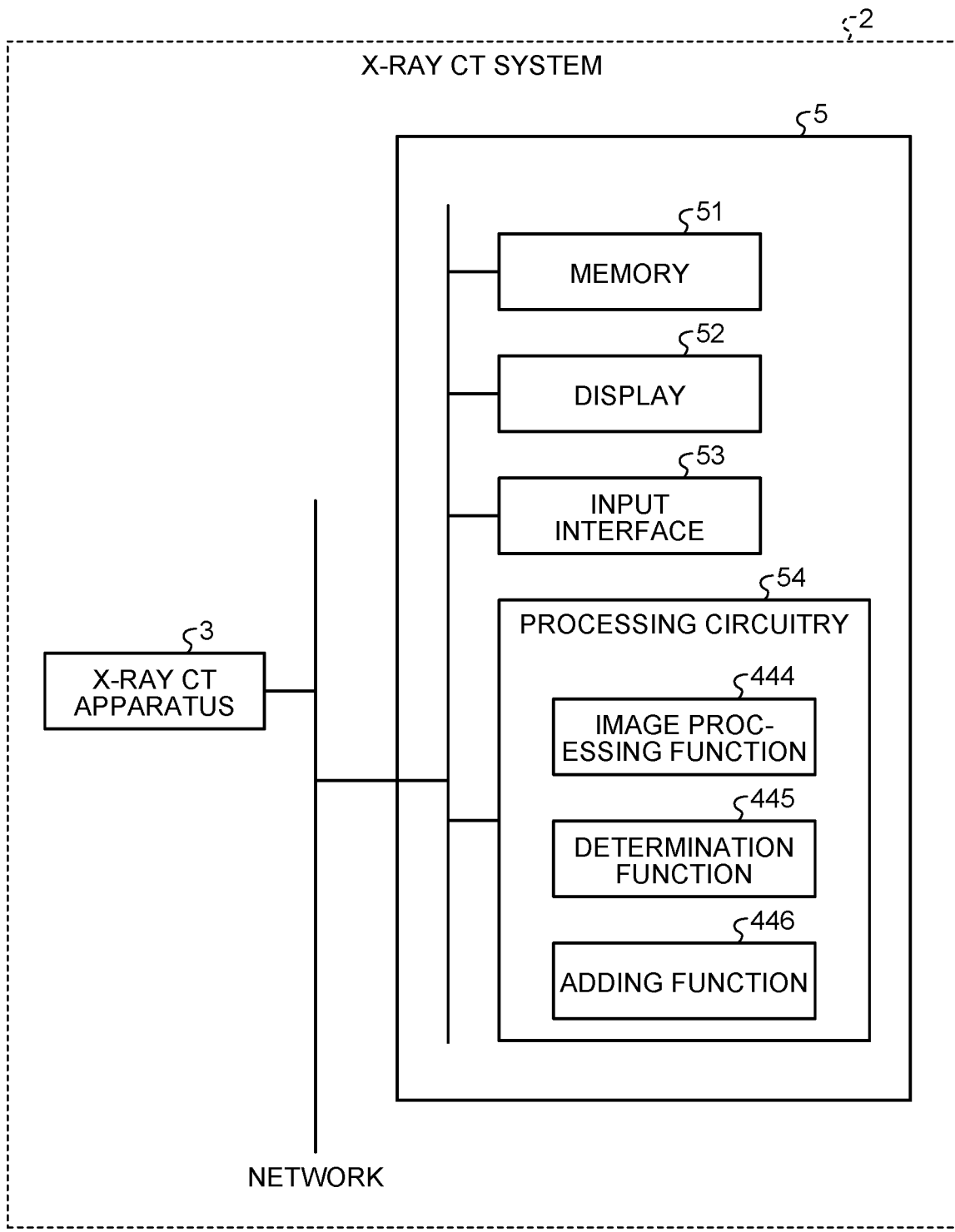
FIG. 12 illustrates an exemplary structure of an X-ray CT system according to a second embodiment.

FIG. 12 illustrates an exemplary structure of an X-ray CT system 2. The X-ray CT system 2 includes an X-ray CT apparatus 3 and a medical image display apparatus 5. The X-ray CT apparatus 3 corresponds to, for example, an existing X-ray CT apparatus excluding the determination function 445 and the adding function 446 of the X-ray CT apparatus 1 illustrated in FIG. 1. Explanation of the X-ray CT apparatus 3 is thus omitted herein. The medical image display apparatus 5 may be incorporated in, for example, a PACS or a HIS, or may be implemented as a terminal apparatus connected to a PACS server or a HIS server. For another example, the medical image display apparatus 5 may function as a radiographic diagnosis terminal.

The medical image display apparatus 5 includes a memory 51, a display 52, an input interface 53, and processing circuitry 54. The memory 51, the display 52, the input interface 53, and the processing circuitry perform data communications with one another via, for example, a bus. The hardware configuration of the memory 51, the display 52, the input interface 53, and the processing circuitry 54 is the same or similar as that of the memory 41, the display 42, the input interface 43, and the processing circuitry 44 in the first embodiment, therefore, a description thereof is omitted. The operational details of the functions of the processing circuitry 54 are the same or similar as those in the first embodiment, so that the differences from the first embodiment are described herein.

The memory 51 stores multiple medical images previously generated by the X-ray CT apparatus 3 (hereinafter, referred to as previous images). The previous images have added thereto supplementary information including software version information of the X-ray CT apparatus 3 having generated the previous images and/or the model number and/or name of the X-ray CT apparatus 3, for example.

The determination function 445 serves to determine the posture of the subject P at the time of a scan with respect to the previous image, based on the supplementary information. As an example, the determination function 445 determines decubitus-position information as the posture when the version information is more previous than a given version. Alternatively, the determination function 445 may determine decubitus-position information as the posture based on the model number or name of the X-ray CT apparatus 3. After failing to determine the posture based on the supplementary information, the determination function 445 determines the posture of the subject P at the time of the scan with respect to the previous image as unknown.

The adding function 446 serves to add posture-related information as to the posture determined by the determination function 445 to the previous image. The adding function 446 may collectively add pieces of posture-related information to the previous image as many as possible.

The display 52 serves to display the previous image in association with posture-related information PRI. For example, the display 52 displays the medical image or the previous image in association with the posture-related information PRI at the time of a radiographic diagnosis of the medical image or the previous image. If the posture-related information added to the previous image indicates "unknown", the display 52 may display "unknown" or a symbol such as a question mark "?" representing "unknown" as the posture-related information, together with the previous image. For another example, in a situation that no universal CT apparatuses or upright CT apparatuses are connected in an in-hospital network or in a coordinated hospital network, the medical image display apparatus 5 may display no posture-related information along with the medical image and the previous image.

Figure 13:
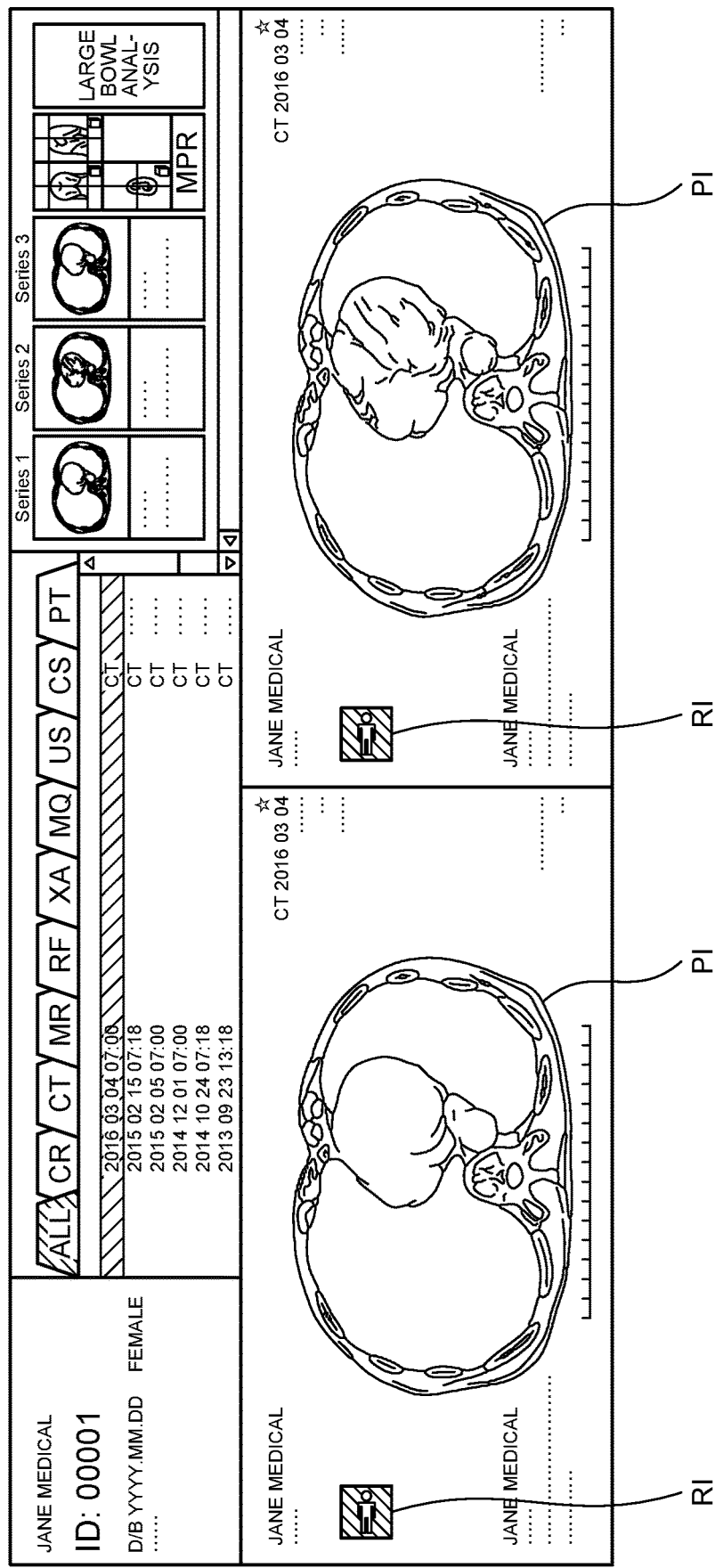
FIG. 13 illustrates a display of exemplary previous images and posture-related information (posture icon) on a display of a medical image display apparatus used as a radiological diagnostic viewer in the second embodiment.

FIG. 13 illustrates an example of a previous image PI and posture-related information (posture icon RI) displayed on the display 52 of the medical image display apparatus 5 used as a radiological diagnostic viewer. As illustrated in FIG. 13, posture icons RI are displayed in the vicinity of the medical images on the display during a radiological diagnosis.

The medical image display apparatus 5 of the second embodiment as described above determines the posture of the subject P at the time of the scan, according to the imaging condition for the scan of the subject P, and displays a medical image reconstructed by the scan in association with information as to the posture. Thereby, in displaying the reconstructed medical image, it is made possible for the operator to easily, with no confusion, determine in what posture the subject has been scanned to capture the medical image without accessing detailed information (e.g., property) on the medical image. This leads to improvement in radiological diagnosis efficiency, for example. The procedure and effects of the posture display process except for scanning are the same or similar as those in the first embodiment, therefore, a description thereof is omitted.

To implement the technical ideas of the embodiments by a medical image display method, the medical image display method includes determining a posture of a subject at the time of a scan, according to an imaging condition reflecting an examination order for the scan of the subject, and displaying a medical image reconstructed by the scan, in association with information as to the posture. The procedure and effects of the posture display process by the medical image display method are the same or similar as those in the first embodiment, therefore, a description thereof is omitted.

To implement the technical ideas of the embodiments by a medical image display program, the medical image display program, when executed by a computer, causes the computer to determine a posture of a subject at the time of a scan, according to an imaging condition reflecting an examination order for the scan of the subject, and to display a medical image reconstructed by the scan on the display 52, in association with information as to the posture. As an example, the posture display process can be implemented by installing the medical image display program on various kinds of server devices (processing devices) that involve the medical image display process and loading the program onto the memories. In this case the program that causes the computer to perform such processing can be stored and distributed in a storage medium such as a magnetic disk (as a hard disk), an optical disc (CD-ROM, DVD, etc.), and a semiconductor memory. The procedures and effects of the medical image display program are similar or same as those of the first and second embodiments, therefore, a description thereof is omitted.

According to at least one of the embodiments as above, it is possible to display the medical image of the subject generated by a scan, in association with information as to the posture of the subject during the scan.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   processing circuitry configured to
      perform reconstruction processing to raw data generated by a scan of a subject to reconstruct a medical image, and
      determine a posture of the subject at a time of the scan according to an imaging condition reflecting an examination order for the scan; and
   a display that displays the medical image in association with information as to the posture, wherein
   the processing circuitry is further configured to convert the medical image into a posture transformed image associated with another posture different from the posture, and
   the display displays the posture transformed image together with information as to the another posture and information representing that the posture transformed image has been converted from the medical image.

2. The X-ray computed tomography apparatus according to claim 1, wherein the display displays at least one of:
   upright-position information and the medical image when the posture is upright,
   decubitus-position information and the medical image when the posture is decubitus, and
   seated-position information and the medical image when the posture is seated.

3. The X-ray computed tomography apparatus according to claim 1, wherein
   the display displays the medical image in a manner that a type of the posture is identifiable.

4. The X-ray computed tomography apparatus according to claim 1, wherein the display
   displays a list in a first display region, the list containing, for each scan, a row of the imaging condition and an icon representing an imaging mode in the scan,
   displays, in a second display region, a medical image associated with a scan selected from the list, and
   displays information as to the posture associated with the scan in the first display region adjacent to the icon.

5. The X-ray computed tomography apparatus according to claim 1, wherein
   the display displays the medical image and the information as to the posture in a display mode which allows an input of a reconstruction condition different from a reconstruction condition for the medical image.

6. The X-ray computed tomography apparatus according to claim 1, wherein
   the processing circuitry is further configured to determine the imaging condition based on the posture, when an examination order for the subject specifies the posture, and
   the display displays the determined imaging condition and information as to the posture included in the examination order.

7. The X-ray computed tomography apparatus according to claim 6, wherein
   with respect to the information as to the posture on display together with the imaging condition, the processing circuitry is further configured to change the imaging condition to another imaging condition associated with a different posture, in response to an instruction for changing the posture to the different posture, and
   the display displays the another imaging condition and information as to the different posture.

8. The X-ray computed tomography apparatus according to claim 1, wherein
   the processing circuitry is further configured to add the information as to the posture to the raw data and the medical image.

9. A medical image display apparatus comprising:
   processing circuitry configured to determine a posture of a subject at a time of a scan, according to an imaging condition reflecting an examination order for the scan of the subject; and
   a display that displays a medical image reconstructed by the scan, in association with information as to the posture, wherein
   the processing circuitry is further configured to convert the medical image into a posture transformed image associated with another posture different from the posture, and
   the display displays the posture transformed image together with information as to the another posture and information representing that the posture transformed image has been converted from the medical image.

10. A medical image display method comprising:
    determining a posture of a subject at a time of a scan, according to an imaging condition reflecting an examination order for the scan of the subject;
    displaying a medical image reconstructed by the scan, in association with information as to the posture;
    converting the medical image into a posture transformed image associated with another posture different from the posture; and
    displaying the posture transformed image together with information as to the another posture and information representing that the posture transformed image has been converted from the medical image.

* * * * *